United States Patent [19]

Jelich et al.

[11] Patent Number: 5,648,495
[45] Date of Patent: Jul. 15, 1997

[54] PROCESS FOR THE PREPARATION OF 5-SUBSTITUTED 2-CHLOROPYRIDINES

[75] Inventors: Klaus Jelich, Overland Park, Kans.; Hans Lindel; Christoph Mannheims, both of Leverkusen, Germany; Reinhard Lantzsch, Wuppertal, Germany; Walter Merz, Leverkusen, Germany

[73] Assignee: Bayer Aktiengesellschaft, Leverkusen, Germany

[21] Appl. No.: 584,867

[22] Filed: Jan. 11, 1996

[30] Foreign Application Priority Data

Jan. 19, 1995 [DE] Germany ............... 195 01 478.2

[51] Int. Cl.$^6$ .................. C07D 213/61
[52] U.S. Cl. .................. 546/250
[58] Field of Search .................. 546/250

[56] References Cited

U.S. PATENT DOCUMENTS

| | | | |
|---|---|---|---|
| 4,504,664 | 3/1985 | Nelson et al. | 546/243 |
| 5,099,025 | 3/1992 | Kaufmann et al. | 546/345 |
| 5,304,651 | 4/1994 | Lantzsch | 546/250 |
| 5,420,284 | 5/1995 | Kraus | 546/250 |

FOREIGN PATENT DOCUMENTS

| | | |
|---|---|---|
| 0490199 | 6/1992 | European Pat. Off. |
| 0546418 | 6/1993 | European Pat. Off. |

OTHER PUBLICATIONS

Chemical Abstracts, abstract No. 158,984b, abstract of DE 4,005,115, (1991).

O. Meth-Cohn, et al., J. Chem. Soc. Perkin Trans. I, pp. 1173–1182, (1984).

Derwent Database, AN 66–31844f, abstract of SU–193519, (1966).

Primary Examiner—C. Warren Ivy
Assistant Examiner—D. Margaret M. Mach
Attorney, Agent, or Firm—Sprung Horn Kramer & Woods

[57] ABSTRACT

The present invention relates to a process for the preparation of 5-substituted 2-chloropyridines of the formula (I)

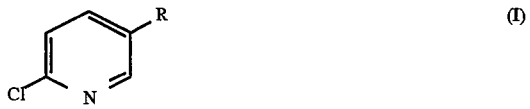

by reaction of acetenamides of the formula (II)

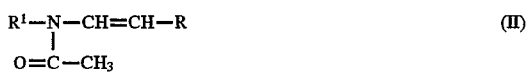

with Vilsmeier reagent, which is prepared by reaction of dialkylformamides of the formula (III)

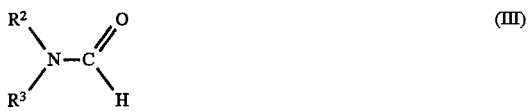

with a chlorinating agent, the excess of which is removed from the reaction mixture by distillation or by addition of dialkylformamide after completion of the reaction of the Vilsmeier reagent with the acetenamide of the formula (II), wherein in the formulae (I)–(III):

R represents optionally substituted alkyl or aralkyl,
$R^1$ represents $C_1$–$C_4$-alkyl or aryl–$C_1$–$C_4$-alkyl,
$R^2$ and $R^3$ represent straight-chain, branched or cyclic $C_4$–$C_8$-alkyl.

4 Claims, No Drawings

PROCESS FOR THE PREPARATION OF 5-SUBSTITUTED 2-CHLOROPYRIDINES

The present invention relates to a process for the preparation of 5-substituted 2-chloropyridines by reaction of dialkylformamides with acetenamides in the presence of chlorinating agents.

European Offenlegungsschrift 546 418 discloses that 5-substituted 2-chloropyridines are accessible from acetenamides by reaction with dimethylformamide in the presence of a chlorinating agent.

In this process, the intermediately formed Vilsmeier salt eliminates the corresponding dimethylamine, which in principle could be reacted to give the formamide again and fed back into the process.

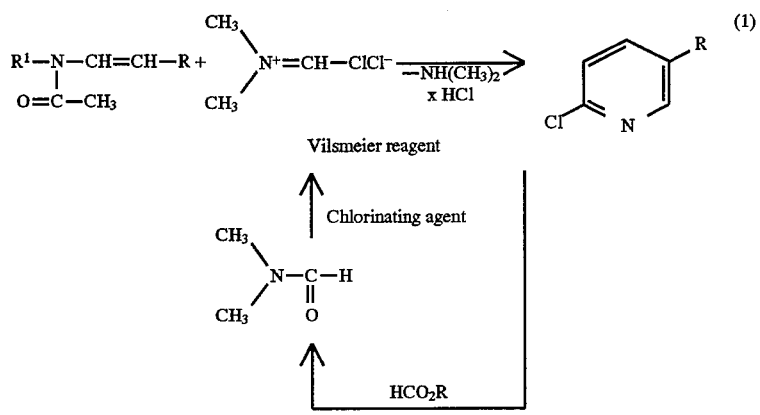

The dimethylamine partially escapes via the gas phase. It is partially present as the hydrochloride and can be lost by reaction with the chlorinating agent:

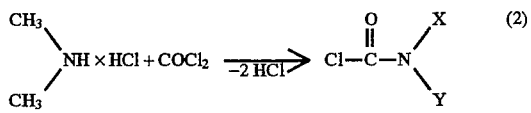

The yield of recyclable dimethylamine is thereby reduced; additionally the resulting carbamoyl chlorides are undesirable reactive by-products.

The present invention relates to a process for the preparation of 5-substituted 2-chloropyridines of the formula (I)

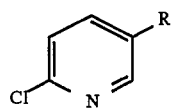

in which

R represents optionally substituted alkyl or aralkyl, by reaction of acetenamides of the formula (II)

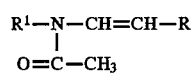

in which

R has the meaning indicated above $R^1$ represents $C_1$–$C_4$-alkyl or aryl-$C_1$–$C_4$-alkyl, with Vilsmeier reagent, which is prepared by reaction of formamides of the formula (III)

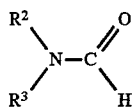

in which $R^2$ and $R^3$ represent straight-chain, branched or cyclic $C_4$–$C_8$-alkyl with a chlorinating agent, the excess of which is removed from the reaction mixture by distillation or by addition of dialkylformamide after completion of the reaction of the Vilsmeier reagent with the acetenamide of the formula (II).

Owing to the use according to the invention of the dialkylformamides of the formula (III), the corresponding dialkylamines are prevented from escaping via the gas phase. As these dialkylamines are not miscible with water, they can also be simply separated from the reaction mixture. Their recovery can additionally be increased by removing the chlorinating agent which has not reacted to form the Vilsmeier reagent from the reaction mixture after completion of the defined reaction.

The process according to the invention preferably relates to the preparation of compounds of the formula (I) in which R represents in each case optionally fluorine- and/or chlorine-substituted $C_1$–$C_6$-alkyl or phenyl-$C_1$–$C_2$-alkyl.

In particular, compounds of the formula (I) are prepared by the process according to the invention, in which R represents methyl, ethyl or benzyl.

Formula (II) provides a general definition of the acetenamides to be used as starting substances. In formula (II), R preferably represents in each case optionally fluorine- and/or chlorine substituted $C_1$–$C_6$-alkyl or phenyl-$C_1$–$C_2$-alkyl, and $R^1$ preferably represents in each case optionally fluorine- and/or chlorine- substituted $C_1$–$C_4$-alkyl or benzyl.

In particular, in formula (II)

R represents methyl, ethyl or benzyl and $R^1$ represents benzyl.

The starting substances of the formula (II) are known and/or can be prepared by processes known per se (cf. J. Chem. Soc. Perkin Trans. I 1984, 1173–1182).

The acetenamides of the formula (II) are obtained, for example, if imines of the general (iv)

in which

R and $R^1$ have the meaning indicated above are reacted with acetic anhydride or acetyl chloride, if appropriate in the presence of an acid acceptor, e.g. triethylamine, and if appropriate in the presence of a diluent, e.g. toluene, at temperatures between 0° C. and 50° C. and the reaction mixture is worked up by customary methods.

The imines of the formula (IV) are known and/or can be prepared by processes known per se (cf. *J. Am. Chem Soc.* 66 (1944), 82–84).

Chlorinating agents which can be employed in the process according to the invention are compounds which with formamides form the so-called Vilsmeier reagent (N,N-disubstituted chloromethylimmonium chloride) (V)

where $R^2$ and $R^3$ have the meaning indicated above.

Suitable formamides are di-n-butylformamide, di-iso-, or di-sec-butylformamide and dicyclohexylformamide, N,N-Di-n-butylformamide is preferred.

The chlorinating agents in particular include acid chlorides which can be removed from the reaction mixture by distillation, such as phosphoryl chloride (phosphorus oxychloride/$POCl_3$), phosgene, oxalyl chloride and thionyl chloride. Phosgene is particularly preferred.

The process according to the invention for the preparation of the 5-substituted 2-chloropyridines of the formula (I) is optionally carried out in the presence of a diluent. Suitable organic solvents are virtually all those which are inert to the reaction. These preferably include aliphatic and aromatic, optionally halogenated hydrocarbons such as hexane, heptane, cyclohexane, methylcyclohexane, benzene, toluene, xylene, chlorobenzene, o-dichlorobenzene, chloroform and tetrachloromethane, and also ethers such as methyl tert-butyl ether, methyl tert-amyl ether and 1,2-dimethoxyethane, and also nitriles such as acetonitrile, propionitrile, n- or iso-butyronitrile. Toluene and chlorobenzene are particularly preferred.

The reaction temperatures can be varied within a wide range in the process according to the invention. The reaction is carried out at temperatures between −30° C. and +160° C., preferably at temperatures between −10° C. and +145° C., in particular in the first reaction phase at 0° C. to 40° C., then at 80° C. to 145° C.

The process according to the invention is in general carried out under normal pressure. However, it is also possible to work at elevated or reduced pressure of between 0.1 bar and 10 bar.

For carrying out the process according to the invention, in general between 1 and 10 mol, preferably between 1.5 and 5 mol, in particular between 2.0 and 3.0 mol, of chlorinating agent and between 1 and 50 mol, preferably between 1 and 1.5 mol, of dialkylformamide are employed relative to 1 tool of acetenamide of the formula (II).

In a preferred embodiment of the process according to the invention, the chlorinating agent and the dialkylformamide are first reacted, preferably by initially introducing the dialkylformamide and slowly adding the chlorinating agent with gentle cooling. The acetenamide of the formula (II) is then slowly metered into this mixture and the reaction mixture is stirred at elevated temperature until the end of the reaction.

In a preferred embodiment, the reagents are added in parallel, e.g. parallel addition of the mixture of dialkylformamide and the acetenamide and phosgene to initially introduced solvent. It is thereby possible to work under highly concentrated conditions—even when using solvents such as chlorobenzene or toluene—since precipitation of solid is avoided. Under these conditions, the chlorinating agent reacts in a virtually addition-controlled manner, whereby accumulation with corresponding risk potential is avoided. As the occurrence of crystalline phases is avoided, it is likewise possible to use a continuous reaction procedure, e.g. in a reactor cascade.

The parallel addition is possible in various ways. The acetenamide can be added in a mixture with the dialkylformamide parallel to the introduction of the chlorinating agent into the initially introduced solvent.

It is likewise possible to add the reagents separately but in parallel.

However, dialkylformamide can also be initially introduced in the solvent and chlorinating agent and the acetenamide metered in parallel.

It is likewise possible to add all reagents, including the solvent, in parallel.

The addition are carried out in a temperature range from approximately −10° C. to +50° C., particularly preferably +10° C. to +40° C.

The mixture is then additionally stirred for a period of from 0.5 to 5 hours, particularly preferably 0.5 to 2 hours, at a temperature of below 50° C.

After addition of the reagents, the mixture is preferably subsequently stirred at temperatures below 50° C. until the reaction of the defined chlorinating agent is finished. The chlorinating agent is then removed by distillation. To do this, the reaction mixture is brought to boiling and the excess chlorinating agent—pure or as a mixture with the solvent used—is distilled off. This is brought about by applying a sufficient vacuum to the reactor at relatively low temperature (below 50° C.) or by adding the mixture in the boiling state to a further reactor via a distillation column with a short residence time in the column, the chlorinating agent being distilled off via the column. The boiling state necessary for the distillation is achieved with an appropriate temperature profile or at normal pressure by applying a suitable vacuum to the column.

A further, less preferred removal of excess chlorinating agent consists in the addition of a suitable reaction component to the chemical reaction. The subsequent addition is preferred here of a certain amount of the dialkylformamide which is in any case employed for the reaction, whereby free chlorinating agent reacts to give the Vilsmeier reagent and as a result the reaction with the dialkylamine is avoided. The dialkylformamide can be isolated from the excess Vilsmeier complex thus formed after the aqueous work-up and recycled. This variant is also suitable for undistillable chlorinating agents.

Following the removal of the excess chlorinating agent, the reaction is finished at an appropriate temperature (80° to 160° C, particularly preferably 100° to 145° C.).

EXAMPLE 1

At an internal temperature of 40° C.

a) mixture of 189 g (1 mol) of N-benzyl-N-(1-propenyl) -acetamide and 172.6 g (1.1 tool) of N,N-di-n-butylformamide and b) 297 g (3 tool) of phosgene are added in parallel to 700 ml of chlorobenzene.

The mixture is stirred at 40° C. for 1 hour. The mixture is then uniformly added via a distillation column to a reaction flask containing 100 ml of boiling chlorobenzene. Addition is carried out in the centre of the column, and a mixture of chlorobenzene and phosgene is continuously distilled off at the top.

| Conditions: | R:F = 10:1 |
|---|---|
|  | 550 mbar |

After addition is complete, the mixture is stirred at 115° C. for 1 hour and the crude mixture (811 g) is analysed against standard:

2-chloro-5-methylpyridine: 14.3 % (91% of theory)
di-n-butylcarbamoyl chloride: 0.4 % (1.7 % of theory)
di-n-butylamine×HCl: 18.8 % (91% of theory).

We claim:

1. Process for the preparation of 5-substituted 2-chloropyridines of the formula (I)

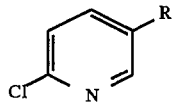 (I)

in which

R represents optionally substituted alkyl or aralkyl, by reaction of acetenamides of the formula (II)

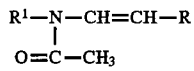 (II)

in which

R has the meaning indicated above represents $C_1$–$C_4$-alkyl or aryl–$C_1C_4$-alkyl, with Vilsmeier reagent, which is prepared by reaction of dialkylformamides of the formula (III)

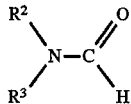 (III)

in which $R^2$ and $R^3$ represent straight-chain, branched or cyclic $C_4$–$C_8$-alkyl with a chlorinating agent, wherein the chlorinating agent, the dialkylformamide and the acetenamide are added at temperatures between −10° C. and 50° C. into an inert solvent, excess chlorinating agent is removed from the reaction mixture and subsequently the reaction is finished by heating at temperatures between 80° and 160° C.

2. Process according to claim 1, wherein the molar ratio of acetenamide of the formula (II) and dialkylformamide of the formula (III) is between 1 to 1 and 1 to 1.5.

3. Process according to claim 1, wherein a mixture of dialkylformamide and acetenamide and also phosgene are added in parallel to an initially introduced solvent.

4. Process according to claim 1, wherein the process is carried out continuously.

* * * * *

UNITED STATES PATENT AND TRADEMARK OFFICE
CERTIFICATE OF CORRECTION

PATENT NO. : 5,648,495
DATED : July 15, 1997
INVENTOR(S) : Jelich, et al.

It is certified that error appears in the above-indentified patent and that said Letters Patent is hereby corrected as shown below:

Col. 6, line 1   Before " represents " insert -- $R^1$ --

Signed and Sealed this

Ninth Day of December, 1997

Attest:

BRUCE LEHMAN

Attesting Officer  Commissioner of Patents and Trademarks